(12) United States Patent
Sachdev

(10) Patent No.: US 9,440,098 B2
(45) Date of Patent: Sep. 13, 2016

(54) ANTIWRINKLE COMPOSITION AND AGE REVERSAL COMPLEX

(76) Inventor: Naina Sachdev, Lake Oswego, OR (US)

(*) Notice: Subject to any disclaimer, the term of this patent is extended or adjusted under 35 U.S.C. 154(b) by 834 days.

(21) Appl. No.: 11/376,207

(22) Filed: Mar. 16, 2006

(65) Prior Publication Data

US 2006/0177407 A1    Aug. 10, 2006

Related U.S. Application Data

(63) Continuation of application No. 10/630,184, filed on Jul. 30, 2003, now abandoned.

(60) Provisional application No. 60/401,555, filed on Aug. 6, 2002.

(51) Int. Cl.
| | | |
|---|---|---|
| *A61K 8/64* | (2006.01) | |
| *A61Q 19/00* | (2006.01) | |
| *A61Q 19/08* | (2006.01) | |
| *A61Q 19/10* | (2006.01) | |

(52) U.S. Cl.
CPC ............... *A61Q 19/08* (2013.01); *A61K 8/64* (2013.01); *A61Q 19/00* (2013.01); *A61Q 19/10* (2013.01)

(58) Field of Classification Search
None
See application file for complete search history.

(56) References Cited

U.S. PATENT DOCUMENTS

| | | | | |
|---|---|---|---|---|
| 4,446,149 A | * | 5/1984 | Nagai | 514/19 |
| 5,306,511 A | * | 4/1994 | Whang | 426/66 |
| 5,334,617 A | * | 8/1994 | Ulrich et al. | 514/562 |
| 5,545,398 A | * | 8/1996 | Perricone | 424/59 |
| 5,690,919 A | * | 11/1997 | Rockl et al. | 424/65 |
| 5,759,584 A | * | 6/1998 | Traupe et al. | 424/520 |
| 5,980,703 A | * | 11/1999 | Yamada et al. | 204/253 |
| 6,284,802 B1 | * | 9/2001 | Bissett et al. | 514/739 |
| 6,358,514 B1 | * | 3/2002 | Boussouira et al. | 424/401 |
| 6,629,970 B2 | * | 10/2003 | Bagrov et al. | 604/521 |
| 7,205,003 B2 | * | 4/2007 | Maibach et al. | 424/722 |
| 2003/0118525 A1 | * | 6/2003 | Grigg | 424/59 |
| 2006/0286046 A1 | | 12/2006 | Haber | |

FOREIGN PATENT DOCUMENTS

| | | | |
|---|---|---|---|
| EP | 0697213 A1 | | 2/1996 |
| EP | 0711552 A1 | | 5/1996 |
| JP | 11137212 A | * | 5/1999 |
| JP | 2002212052 A | * | 7/2002 |
| WO | WO 9006102 A | * | 6/1990 |

OTHER PUBLICATIONS

STN online, file CIN, Acc. No. 26(34):37966G (Financ. Times (North Am. Ed.) (1997), "Breakthrough in care of ageing skin", p. 17), Abstract.*
Tamba et al., Int. J. Radiat. Biol. (1998), vol. 74, No. 3, pp. 333-340.*
STN online, file BIOSIS, Acc. No. 2000:324873 (Hipkiss et al., CMLS Cellular and Molecular Life Sciences (2000), vol. 57, No. 5, pp. 747-753), Abstract.*
Jordan, Carnosine Nature's pluripotent life extension agent, Life Extension Magazine (Jan. 2001), pp. 1-5 of 5.*
Ananthapadmanabhan KP et al. 2003. pH-induced alterations in stratum corneum properties. Intl J Cosmetic Sci. 25:103-112.
Feingold, KR. 2007. The role of epidermal lipids in cutaneous permeability barrier homeostasis. J Lipid Res 48:2531-2546.
Schmid, M. 1995. The concept of the acid mantle of the skin. Dermatology 191:276-280.
Fluhr, JW. 2001. Generation of Free Fatty Acids from Phospholipids Regulates Stratum Corneum Acidification and Integrity. J Invest Dermatology 117:44-51.
Hachem, J-P. 2003. pH directly regulates epidermal permeability barrier homeostasis and stratum corneum integrity/cohesion. J InvestDermatol 121:345-353.
Aruoma, IO. 1998. Carnosine, homocarnosine and anserine: could they act as antioxidants in vivo? Biochem J 264:863-869.

* cited by examiner

*Primary Examiner* — Abigail Fisher
*Assistant Examiner* — Frank Choi
(74) *Attorney, Agent, or Firm* — Robert L. Stone

(57) ABSTRACT

An alkaline anti-wrinkling composition comprising carnosine, derivative thereof, or mixture of carnosine, and derivative thereof.

4 Claims, No Drawings

ANTIWRINKLE COMPOSITION AND AGE REVERSAL COMPLEX

This application is a continuation of U.S. patent application Ser. No. 10/630,184, filed on Jul. 30, 2003, now abandoned, which claims the benefit of U.S. Provisional Application No. 60/401,555, filed on Aug. 6, 2002.

BACKGROUND OF THE INVENTION

This invention relates to a cosmetic composition contain carnosine that is highly effective in controlling the ageing process by reversing, preventing and reducing wrinkling of skin. In particular the invention includes a complex containing carnosine that is especially effective in reversing, preventing and reducing the aging process that is visually observable through the formation of skin wrinkles. During the aging process glycated end products of bonding between protein material and sugar molecules naturally leads to formation of deep wrinkles in the skin that are particularly visible in normally exposed areas such as the face. Without being bound to the reasons for the effectiveness of the product of the present invention, it is theorized that carnosine prevents, reduces and can reverse the formation of such glycated end products and also breaks the protein-sugar bonds to enable actual reversal of skin wrinkles. If glycosylation were not prevented it would proceed as follows: a. sugar/aldehyde molecules approach protein molecules (for instance, malondialdehyde could approach, attach to and inactivate healthy protein molecules); b. sugar molecules attach to protein molecules leading to carbonylation crosslinking; c. the proteins that are carbonylated crosslinks (a detrimental factor); and d. advanced glycosylation end products (AGE's) form, which can cause extensive damage by reacting with free radicals and other toxins so that AGE's deposit in the cell structure (it is noted in this regard that malondialdehyde is the result of free radical damage to lipids, the fatty portion of cells, leading to a vicious cycle of aging (observed by skin wrinkling) since oxidation results in free radical formation that produces malondialdehyde, causing glycosylation that results in AGE's leading to more free radicals to repeat the process).

Prior research has determined that carnosine, with its known anti-glycating properties, may provide an anti-aging effect on fibroblast material by inhibiting cross-liking of glycoxidized proteins (Hipkiss et al. Mech. Ageing Dev., Sep. 15, 2000, 122(13), p. 1431-1445). Carnosine is reactive as an anti-glycating agent with aldehydes and ketones, that is compounds containing carbonyl groups (Hipkiss et al. Cell Mol. life Sci., May, 2000, 57 (5), p. 747-753 capable of blocking carbonylated proteins, that form in step b., describe above, and thus prevent the formation of detrimental AGE's.

Carnosine and complexes containing carnosine have been described in skin care compositions and to promote wound healing, as in U.S. Pat. No. 5,091,171 to Yu et al; U.S. Pat. No. 5,723,482 to Degwert et al; U.S. Pat. No. 5,606,588 to Zaloga et al; and U.S. Pat. No. 4,981,846 to Matsukura et al. It is noteworthy, with particular regard to the patent to Yu et al, that while various cosmetic effects are disclosed for compositions containing an alpha-hydroxyacid or alpha-ketoacid and various amphoteric materials, including dipeptides. It is specifically disclosed that although the presence of alkali (ammonium hydroxide) does permit the composition to be therapeutic for dry skin, it loses much of its potency against wrinkles. Carnosine is disclosed among the dipeptides set forth. However, the patent does not recognize that it could be effective against skin wrinkles under alkaline conditions.

It is an advantage of this invention that an alkaline skin cosmetic composition is provided that is topically applied and transdermally effective against wrinkling of skin.

It is a further advantage of this invention that the antiwrinkle composition contains carnosine, derivatives thereof or mixtures of carnosine and derivatives thereof.

It is a further advantage of this invention that the carnosine and/or its derivatives are present in a complex that can be observed to reverse, prevent and reduce the aging process with regard to reversing, preventing and reducing formation of skin wrinkles.

Additional advantages resulting from the use of carnosine, including its derivatives include:
1. Ability to combine with sugar aldehydes such as malondialdehyde and inactivate them, thereby preventing carbonylation crosslinking;
2. As antiglycosylating agents they are superior in activity against free radicals to usual antioxidants, such as Vitamins E and C and the like that are not antiglycosylating agents;
3. They are antiglycosylating nutrients;
4. They inactivate free radicals within the cell after their formation,
5. They increase elimination of materials already damaged by free radicals;
6. They are effective against chronic inflation
7. They act as chelating agents to bind heavy metals and inactivate them, as well as assisting In regulating the concentration of these heavy metals (especially zinc and copper) to raise or lower the concentrations to desired levels;
8. They have antioxidant effect by stabilizing cell membranes and preventing free radical damage especially to the cell membranes;
9. They reduce or block excessive nitric oxide activity by blocking activation of guanylate cyclase, which is normally activated by nitric oxide.

It is a further advantage of this invention that the alkaline composition is compatible with other cosmetically desirable components, particularly non-allergenic components.

Additional advantages will be apparent from consideration of the following specification.

BRIEF DESCRIPTION OF THE INVENTION

In accordance with certain of certain of its aspects, this invention relates to an alkaline cosmetic composition having a pH of about 7.5 to about 9.5 that is effective against skin wrinkling, said composition comprising carnosine, derivatives thereof and mixtures of carnosine and derivatives thereof dispersed in an alkaline cosmetically acceptable vehicle in effective antiwrinkle amount up to about 50% by weight of carnosine

DETAILED DESCRIPTION OF THE INVENTION

Carnosine is a naturally occurring dipeptide composed of β-alamine and histidine and has a molecular weight of 226.24. It is commonly found in brain and innervated tissues and the ocular lens. Advantages obtained with the use of carnosine in the present invention are not characteristics of β-alanine and histidine, even when use in mixture with each other. It may be employed in its α- and β-forms as well as mixtures thereof. The α-form (also called L-carnosine) is preferred and the most readily available. It is most preferably used in its uncomplexed form although it may in a complex salt or salts, for instance with zinc, copper or manganese or in uncomplexed or such complex salts of derivative compounds, such as N-acetylcarnosine, which is a lipid soluble acid. When this lipid soluble acid is used, the pH range of about 7.5 to about 9.5 is maintained with use of alkaline water in the composition or by buffers. Other derivatives of carnosine included in the present invention are anserine (that is mediation of carnosine), homocarnosine, N-α-acetylcarnosine, carcinine and numerous variants that are imidazole di-peptides, Such derivatives are described in the book, Carnosine And Other Elixirs of Youth—The Miraculous Anti-Ageing Supplement, Kyriazis, 2003, Watkins Publishing, London. (Carnosine, a derivative thereof or mixture of carnosine and derivative thereof is employed in the cosmetic composition in an effective antiwrinkle amount typically about 0.5% to about 50% that is about 5 mg/ml to about 500 m/ml of composition), preferably about 1.5% to about 30% and most preferably about 10% to about 20% by weight Additional ingredients that cooperate with and are compatible with carnosine to achieve nutrient balance and improve anti-wrinkle effectiveness include cascading antioxidants such as rosemarinic acid (that is, carnosac acid or caronsol embilica and additional polyphenol antioxidants, as well as anti-inflammatory materials such as beta-glucan, alkyl alcohol amines and the like. In this regard, it is noted that carnosine possesses antioxidant and anti-inflammatory properties.

It is also desirable to provide carnosine or its derivative either as such or as a complex salt and a complex composition that contains one or more of penetration enhancers of skin such as phosphotidyl, choline, serine and 1-theanine, neutralizing agents for reactive radicals such as tocotreniols, especially in the gamma form, γ-tocophenol and mixed α-, β- and γ-tocotreniols, anti-inflammatory agents such as glycerhizinate of licorice extract, cell stimulants such as glutathione and kinetin, growth promoting and bio-activating agents such as L-tyrosine and N-acetylcystine, and enhancers of the immune system such as clostrum and lactoferrin. Synergistic effects can be observed with the carnosine complex.

Typical concentrations for these compatible additives are about 0.1% to about 5.0% by weight of antioxidants, about 0.1% to about 10% by weight of anti-inflammatory, about 0.1% to about 10% by weight of skin penetrating agents, about 0.1% to about 5% by weight of neutralizing agents of reactive radicals, about 0.1% to About 2% by weight of anti-inflammatory agents, about 1% to about 5605 by weight of each of cell stimulants, growth promoting and bio-activating agents, and immune system enhancers. The carnosine compositions and the carnosine complexes can be employed in topically applied cosmetic compositions such as those applied to the skin in daytime, at nighttime, to tone the skin, to wash skin surfaces such as the face as well as periorbitally around the eyes.

Water, adjusted to a pH of about 7.5 to about 9.5, preferably about 8.0 to about 8.5, is a desirable vehicle for carnosine and other active components. Carnosine and other ingredients, if present, are dispersed in the alkaline aqueous vehicle under ambient conditions. The vehicle may desirably also contain a humectant such as glycerine or sorbitol, typically in amount of about 1% to about 10% by weight. The vehicle may also be an emulsion with a lipid component such as liquid paraffin, squalene, glycerol distearate and the like present in a typical amount of about 0.001% to about 50% by weight. The entire composition is readily prepared free of allergenic components. When carnosine or derivative thereof is present with water only the composition is a suspension.

Carnosine is particularly effective in preventing and reducing wrinkling of skin and may be effective in removing wrinkles as welt due to its excellent anti-glycation properties and ability to break crosslinks associated with wrinkled skin or to prevent them from forming. The effectiveness of carnosine as a wrinkle care material is quite unique to it in comparison to other amino acids including simple amino acids such as alanine and histidine and polypeptides including dipeptides such as glycylglycine and the like.

Carnosine and the various other ingredients described above, that may be present together with other additives that provide nutrients to the skin and for other purposes well known in the art, may be present for treating epidermis (surface) and dermis (deep) (layers such as those described for wrinkle-care products in U.S. Pat. No. 5,939,078 to Fujimura et al. the disclosure of which is incorporated herein by reference.

Such incorporated other additives typically may comprise about 0.001 to about 50% by weight of the cosmetic composition and may include: humectants, ultra oily components, such as hydrocarbons, esters, high carbon fatty acids (e.g. stearic), high carbon alcohols (e.g. stearyl) and sphingosine derivatives from natural sources, typically in amount of about 0.005 to about 30% by weight; sterols, typically in amount of about 0.005 to about 30% by weight; surfactants, especially nonionic surfactants, typically in amount of about 0.005 to about 30% by weight; water-soluble polyhydric alcohols, typically in amount of about 0.1 to about 25% by weight; powders, typically in amount of about 0.001 to about 50% by weight;

silicones, typically in amount of about 0.005 to about 30%; as well as minor amounts of non-deteriorating salts, thickeners, pH regulators, violet absorbers, coloring agents, medicinal components, perfumes and the like. Other additives are included in the illustrative examples below.

The invention is illustrated by the following illustrative examples. All amounts and ranges are by in parts by weight unless otherwise indicated.

Example 1

The anti-wrinkling composition set forth below is prepared by dispersing the several ingredients with stirring in the alkaline aqueous vehicle.

| Component | Parts |
| --- | --- |
| L-carnosine | 25 |
| Gamma-tocotreniol | 5 |
| Licorice root | 1 |
| Embilica | 1 |
| L-theanine | 10 |
| Glutathione | 10 |
| L-tyrosine | 5 |
| L-acetylcysteine | 2 |
| Clostrum | 1 |
| Lactoferrin | 1 |
| Deionized water (buffered to | Q.S. to 100 |
| (buffered to with aminometylpropanol, triethanolamine, monoisopropanolamine and dimethylmonoethanolamine) | pH 8.0 |

The above composition is topically applied to skin. It is effective to reverse ageing by reducing wrinkles on wrinkled skin when applied to the skin in a regimen twice a day after for two weeks.

The pH of the above composition may be varied using alkaline water and varying the pH with the buffer in the range of 7.5 to 9.5.

Example 2

The composition of Example 1 is prepared except that N-acetylcarnosine replaces carnosine. Again, skin wrinkling is reduced.

Example 3

A suspension containing 35 parts of carnosine in water buffered at pH 7.5 to 8.0 is prepared and is effective to reduce skin wrinkles.

Example 4

The following compositions (A-G) are applied during daytime hours for anti-wrinkling effectiveness and include age-reversal complex ingredients.

| | Parts | | | |
|---|---|---|---|---|
| Ingredient | 4A | 4B | 4C | 4D |
| Phosphatidyl Choline | 0.20 | 0.50 | 2.00 | 0.20 |
| Sodium Hyaluronate | 0.50 | 0.10 | 0.10 | 0.10 |
| Sugarcane Extract | 0.10 | 0.10 | 0.10 | 0.10 |
| EDTA-Na$_2$* | 0.10 | — | — | 0.10 |
| Zinc Sulfate | — | — | — | 0.10 |
| Na Carboxymethyl Betaglucan | 0.10 | — | — | — |
| Xanthan Gum | — | — | — | — |
| Panthenol | 0.05 | — | — | — |
| Et-hexyl Methoxycinnamate | 7.00 | 7.00 | 7.00 | 7.00 |
| Benzophenone-3 | 6.00 | 6.00 | 6.00 | 6.00 |
| Isopropyl Palmitate | — | — | — | 5.00 |
| Cetearyl Alcohol/ceteaarth-20 | — | — | — | 3.00 |
| Cetearyl Alcohol 50/50 | 3.75 | 3.75 | 3.75 | 0.50 |
| Glyceryl Stearate/PEG* 100 Stearate | — | — | — | 1.00 |
| Cetyl Esters | 3.75 | 3.75 | 3.75 | — |
| Sorbitan Stearate | 1.50 | 1.50 | 1.50 | — |
| Tetradecyl Ascorbate | 0.10 | 0.25 | 0.50 | 0.10 |
| Mg Boroascorbate-VDF | — | — | 0.25 | 0.20 |
| Vitamin A Palmitate | 0.05 | 0.10 | — | — |
| Tocotrienol R40 (Vitamin E) | 0.10 | 0.20 | 0.50 | 0.10 |
| Polysorbate 60 | 1.50 | 1.50 | 1.50 | — |
| Ubiquinone (Ubidecarenone) | 0.01 | — | — | — |
| Super Oxide Dismutase | 0.05 | — | — | — |
| PEG*-40 Castor Oil | 0.25 | 1.50 | 1.50 | — |
| Squalane | 1.00 | — | — | — |
| Benzyl Alcohol | 1.50 | 1.50 | 1.50 | — |
| Phenoxyethanol & Me, Et, But, Pro & Isobut Parabens | — | — | — | 0.25 |
| Rosemary Extract | — | 0.20 | 0.50 | 0.20 |
| L-Carnosine | 15.00 | 15.00 | 15.00 | 15.00 |
| L-Theanine | 2.50 | 2.50 | — | — |
| Green Tea Extract-VDF | 0.05 | — | — | — |
| Grape Seed Extract-VDF | 0.05 | — | — | — |
| Vitamin K (powder) | 0.05 | 0.10 | 0.10 | 0.10 |
| Colostrum (powder) | 0.05 | 0.05 | 0.05 | 0.05 |
| Emblica (powder) | 0.10 | 0.05 | 0.05 | 0.05 |
| Licorice (powder) | — | — | — | — |
| Mn Gluconate · 2H$_2$O | 0.05 | 0.05 | 0.05 | 0.05 |
| N-Acetyl L-Cysteine | — | 0.01 | 0.01 | 0.01 |
| Dimethylethanolamine | 0.10 | 0.15 | 0.15 | 0.15 |
| Bergamot Oil | — | 0.001 | 0.001 | 0.001 |
| Water (@ pH 8.0) q.s. | 100 | 100 | 100 | 100 |

*EDTA Na$_2$ is disodium ethylene tetraacetic acid/PEG is polyethylene glycol

| | Parts | | |
|---|---|---|---|
| Ingredient | 4E | 4F | 4G |
| Soy Lecithin | — | — | 0.30 |
| Phosphatidyl Choline | 0.10 | 0.10 | 0.20 |
| Sodium Hyaluronate | 4.00 | 4.00 | 4.00 |
| EDTA-Na$_2$ | 0.10 | 0.10 | 0.10 |
| Zinc Sulfate | — | — | 0.10 |
| Na Carboxymethyl Betaglucan | — | — | 0.20 |
| Xanthan Gum | — | — | 0.10 |
| Et-hexyl Methoxycinnamate | 7.00 | 7.00 | 7.50 |
| Benzophenone-3 | 6.00 | 6.00 | 6.00 |
| Isopropyl Palmitate | 5.00 | 5.00 | — |
| Cetearyl Alcohol/ceteaarth-20 | 3.00 | 3.00 | — |
| Cetearyl Alcohol 50/50 | 0.50 | 0.50 | 3.75 |
| Glyceryl Stearate/PEG 100 Stearate | 1.00 | 1.00 | — |
| Cetyl Esters | — | — | 3.75 |
| Sorbitan Stearate | — | — | 1.50 |
| Tetradecyl Ascorbate | 0.25 | 0.25 | 0.10 |
| Mg Boroascorbate-VDF | 0.20 | 0.20 | — |
| Vitamin A Palmitate | — | — | 0.10 |
| Tocotrienol R40 | 0.50 | 0.50 | 0.10 |
| Polysorbate 60 | — | — | 1.50 |
| Squalane | — | — | 0.20 |
| Benzyl Alcohol | — | — | 1.50 |
| Phenoxyethanol & Me, Et, But, Pro & Isobut Parabens | 0.30 | 0.30 | — |
| Rosemary Extract | 0.30 | 0.30 | — |
| L-Carnosine | 15.00 | 5.00 | 15.00 |
| L-Theanine | — | — | 2.50 |
| Vitamin K (powder) | 0.10 | 0.10 | — |
| Colostrum (powder) | 0.05 | 0.05 | 0.30 |
| Emblica (powder) | 0.05 | 0.05 | 0.10 |
| Licorice (powder) | — | — | 0.10 |
| Manganese Gluconate · 2H$_2$O | 0.05 | 0.05 | — |
| N-Acetyl L-Cysteine | 0.01 | — | — |
| Dimethylethanolamine | 0.15 | 0.15 | 0.40 |
| Bergamot Oil | 0.001 | 0.001 | — |
| Water (@ pH 8.0) q.s. | 100 | 100 | 100 |

*EDTA Na$_2$ is disodium ethylene diamine tetraacetic acid/PEG is polyethylene glycol An aqueous pre-mix is prepared using Water, Phosphatidyl Choline and Sodium Hyaluronate as its base. Normally this aquous pre-mix is heated to approximately 60° C. to facilitate the dissolution of Phosphatidyl Choline. Other components of this premix—Soy Lecithin, Sugarcane Extract, EDTA-Na$_2$, Zinc Sulfate, Na Carboxymethyl Betaglucan, Xanthan Gum, Emblica and Panthenol—are added in different combinations to vary the characteristics of the aqueous phase and final product.

A non-aqueous premix is also prepared with Et-hexyl Methoxycinnamate, Benzophenone-3, Cetearyl Alcohol 50/50, Tetrahexyldecyl Ascorbate and Tocotrienol R40 as its base. Normally this non-aqueous premix is heated until all components are melted and dispersed throughout the premix (~60° C.). Isopropyl Palmitate, Cetyl Alcohol/Ceteareth-20, Glyceryl Stearate/PEG 100 Stearate, Cetyl Esters, Sorbitan Stearate, Vitamin A Palmitate, Squalane, Mg Boroascorbate, Polysorbate 60, Ubiquinone (Ubidecarenone). Super Oxide Dismutase and PEG-40 Castor Oil are added in different combinations to vary the characteristics of the non-aqueous phase and final product.

After these two pre-mixes are prepared and heated, they are combined and the resulting mixture is stirred in order to achieve complete dispersion. It is then allowed to cool. Either Benzyl Alcohol or Phenoxyethanol & Me, Et, But. Pro & Isobut Parabens, used as a preservative system, is added to the cooling dispersion before the addition of L-Carnosine. To the resulting cooling dispersion, Vitamin K (powder), Colostrum (powder), Emblica (powder) and Manganese Gluconate.2H$_2$O are added in various combinations, as is Dimethylethanolamine, that is DMEA (to adjust the pH), along with the other remaining chosen ingredients (L-Theanine, Licorice Powder, Green Tea Extract-VDF, Grape Seed Extract-VDF, N-Acetyl L-Cysteine, Lavender Oil Fragrance and Bergamot Oil).

Upon reaching room temperature, the resulting cream is packaged

It is desirably applied one or two times a day over a two week period.

Example 5

The following compositions (A-C) are applied during nighttime hours for anti-wrinkling effectiveness and include age-reversal complex ingredients (A and B are the most active; C is a simpler formula).

|  | Parts | | |
| --- | --- | --- | --- |
| Ingredient | 5A | 5B | 5C |
| Sodium Hyaluronate | 0.10 | — | — |
| Hydrolyzed Glycosaminoglycans | 0.10 | — | — |
| Sugarcane Extract | 0.05 | — | — |
| EDTA-Na$_2$ | 0.10 | 0.10 | 0.10 |
| Phoshatidyl Choline | — | 4.00 | — |
| Na carboxymethyl Betaglucan | 0.05 | — | 0.05 |
| Isopropyl Palmitate | 6.25 | 6.25 | 6.25 |
| Rice Bran Oil | — | 1.00 | — |
| Cetearyl Alcohol/Ceteareth-$_{20}$ mix | 3.75 | 3.75 | 3.75 |
| Cetearyl Alcohol 50/50 | 0.60 | 0.60 | 0.60 |
| Glyceryl Stearate/PEG 100 Stearate | 1.25 | 1.25 | 1.25 |
| Tetrahexyldecyl Ascorbate | 0.10 | 0.10 | 0.50 |
| Vitamin A Palmitate | 0.05 | 0.10 | 0.01 |
| Butylated Hydroxytoluene | 0.30 | — | 0.30 |
| PEG-40 Hydrogenated Castor Oil | 0.25 | 0.25 | 1.00 |
| Tocotrienol R40 (Vitamin E) | 0.05 | 0.10 | — |
| Ubiquinone (Ubidecarenone) | 0.05 | — | — |
| Super Oxide Dismutase | 0.05 | 0.05 | — |
| Mg Boroascorbate (VDF) | — | 0.10 | — |
| Squalane | 1.00 | — | — |
| Phenoxyethanol & Me, Et, but, Pro. & Isobut Parabens | 0.20 | 0.20 | 0.20 |
| L-Carnosine | 15.00 | 15.00 | 15.00 |
| L-Theanine | 1.00 | — | 1.00 |
| Green Tea Extract - VDF | 0.05 | 0.05 | — |
| *Aloe Vera* (200:1) Extract (Powder) | 0.05 | — | — |
| Colostrum (powder) | 0.05 | 0.05 | — |
| *Emblica* (powder) | 0.10 | 0.10 | — |
| Manganese Gluconate · 2H2O | 0.05 | 0.05 | — |
| Dimethylethanolamine | 0.10 | 0.20 | 0.20 |
| Bergamot Oil | — | — | <0.01 |
| Water @pH 8.0 q.s. | 100 | 100 | 100 |

An aqueous pre-mix is prepared using Water and EDTA-Na$_2$ (Na Carboxymethyl Betaglucan, Phosphatidyl Choline, Sugarcane Extract, Sodium Hyaluronate and Hydrolyzed Glycosaminoglycans are added in different combinations during the heating phase.) This aqueous pre-mix is heated to approximately 60° C.

A non-aqueous pre-mix is also prepared using Isopropyl Palmitate, Cetearyl Alcohol/Ceteareth-$_{20}$, Cetearyl Alcohol 50/50, Glyceryl Stearate/PEG 100 Stearate, T trahexyldecyl Ascorbate, Vitamin A Palmitate and PEGAO Hydrogenated Castor Oil as its base. Normally this non-aqueous pre-mix was heated until all components are m ited and dispersed throughout the pre-mix (at approximately 60° C.). For the 'active' non-aqueous premix, Squalane, Tocotrienol R40, Ubiquinone (Ubidecarenone), Super Oxide Dismutase, Butylated Hydroxytoluene and PEG40 Castor Oil (hydrogenated) are also added in various combinations to the mixture.

After the aqueous and non-aqueous pre-mixes are prepared and heated, they are combined and the resulting mixture is stirred in order to achieve complete dispersion. It is then allowed to cool. Phenoxyethanol & Me, Et, But, Pro & Isobut Parabens, used as a preservative system, is added to the cooling dispersion before the addition of L-Carnosine and L-Theanine. Dimethylethanolamine (DMEA) is added to adjust the pH in both dispersions, although it is added after the other remaining ingredients in the formulation (Green Tea Extract-VDF, Aloe Vera (200:1) Extract (Powder), Colostrum (powder), Emblica (powder), Mg Boroascorbate (VDF) and Manganese Gluconate.2 H2O in varying combinations). As a final step in the cooling 'simple' dispersion Bergamot Oil is added.

Upon reaching room temperature, the resulting cream was packaged. It is desirably applied at night over a two week period.

Example 6

The following compositions (A & B) are applied to tone the skin while providing anti-wrinkling effectiveness and included age-reversal complex ingredients.

|  | Parts | |
| --- | --- | --- |
| Ingredient | A | B |
| L-Carnosine | 1.00 | 5.00 |
| L-Theanine | 0.10 | — |
| Allantoin | 0.05 | 0.10 |
| Na PCA (Pyrocarboxylic Acid Na) | 0.10 | 0.25 |
| Sorbitol (70%) | 0.25 | 0.10 |
| *Aloe Vera* (200:1) Powder | 0.05 | 0.01 |
| Actiphyte of Witch Hazel | 1.00 | 0.50 |
| Actiphyte of *Echinacea* | 1.00 | 0.50 |
| Actiphyte of Chamomile | 1.00 | 0.50 |
| EDTA-Na$_2$ | 0.10 | 0.05 |
| PEG-60 Castor Oil (hydr) | 0.05 | 0.05 |
| Bergamot Oil | 0.05 | 0.01 |
| Phenoxyethanol & Me, Et, Bu, Pro, & Isobut Parabens | — | 0.10 |
| Pentylene Glycol | — | 0.10 |
| Water (@ pH 8.0) q.s. | 100 | 100 |

To the water, which is at room temperature, is added each of the other ingredients, one at a time, allowing for each to dissolve before the addition of the next. The additions are done while the aqueous solution is being stirred.

After sufficient stirring to insure a uniform solution, the resulting toner is packaged. It is desirably applied one to two times a day over a two week period.

Example 7

The following composition is applied to the face as a soft facial wash with anti-wrinkling effectiveness and includes age-reversal complex ingredients.

| Ingredient | Parts |
|---|---|
| Mackadet EQ-76 | 52.00 |
| (Deionized water & PEG 80 Sorbitan Laurate, Cocamidopropyl Na Tridecadeth Sulfate, Na betaine Lauroamphoacetate PEG 150 Distearate, Na laureth-13 Carboxylate PEG 150 Distearate, Citric Acid, Quaternium 15 & Na EDTA) | |
| L-Carnosine | 5.00 |
| Na PCA (Pyrocarboxylic Acid Na) | 0.10 |
| Jojoba Oil (Boston Jojoba) | 0.01 |
| Sugarcane Extract | 0.25 |
| Dimethanolethanolamine | 0.15 |
| Pomelo 7713 (Fragrance) | 0.15 |
| DMDM$_4$ Hydantoin | 0.15 |
| Water q.s. | 100 |

The water is heated to ~45° C. and the following ingredients are added one at a time to the water, with stirring, allowing enough time for dissolution of the previous ingredient Mackadet EQ-76, L-Carnosine, Na PCA, Jojoba Oil (Boston Jojoba) and Sugarcane Extract. The aqueous solution is cooled to room temperature at which the remaining ingredients (Dimethylethanolamine, that is DMAE), Pomelo 7713 and DMDM Hydantoin) are added with stirring, allowing enough time for dissolution of the previous ingredient.

After sufficient stirring to insure a uniform solution, the resulting skin wash is packaged. It is desirably applied to wash the face once a day over a period of two weeks.

Example 8

The following compositions (A & B) are applied periorbitably around the eyes for their anti-wrinkling and age-reversal effects, preferably once daily over a two week period.

| | Parts | |
|---|---|---|
| Ingredient | 8A | 8B |
| Phosphatidyl Choline | 0.20 | 1.00 |
| Sodium Hyaluronate | 4.00 | 0.50 |
| EDTA-Na2 | 0.10 | 0.10 |
| Panthenol | 0.10 | 0.10 |
| Mg Boroascorbate-VDF | — | 0.25 |
| Ethylhexyl Methoxycinnamate | 5.00 | 5.00 |
| Cetearyl Alcohol 50/50 | 3.75 | 3.75 |
| Cetyl Esters | 3.75 | 3.75 |
| Sorbitan Stearate | 1.50 | 1.50 |
| Polysorbate 60 | 1.50 | 1.50 |
| Squalane | 0.10 | — |
| Ceramide- III | 0.10 | 0.10 |
| Tocotrienol R40 (Vitamin E) | 0.10 | 0.20 |
| Ubiquinone (Ubidecarenone) | 0.10 | 0.10 |
| Super Oxide Dismutase | 0.10 | 0.10 |
| Vitamin A Palmitate | 0.05 | 0.05 |
| Tetrahexyldecyl Ascorbate | 0.10 | 0.10 |
| Benzyl Alcohol | 1.50 | 1.50 |
| L-Carnosine | 10.00 | 10.00 |
| L-Theanine | 0.50 | 0.50 |
| Vitamin K (powder) | 0.05 | 0.05 |
| Green Tea Extract - VDF | 0.05 | 0.05 |
| Colostrum (powder) | 0.10 | 0.10 |
| Cucumber Extract | 0.10 | 0.10 |
| Dimethylethanolamine | 0.15 | 0.20 |
| Water (@ pH 8.0) q.s. | 100 | 100 |

An aqueous pre-mix is prepared using Water, Phosphatidyl Choline, Sodium Hyaluronate, EDTA-Na$_2$ and Panthenol as its base. Normally this aqueous pre-mix is heated to at approximately 60° C. to facilitate the dissolution of Phosphatidyl Choline. Mg Boroascorbate is added to one of the formulations but not to the other.

A non-aqueous pre-mix was also prepared with Ethylhexyl Methoxycinnamate, Cetearyl Alcohol 50/50, Cetyl Esters, Sorbitan Stearate, Polysorbate 60, Ceramide III, Tocotrienol R40, Ubiquinone (Ubidecarenone), Super Oxide Dismutase, Vitamin A Palmitate and Tetrahexyldecyl Ascorbate as its base. This non-aqueous pre-mix is heated until all components are melted and dispersed throughout the premix (at approximately 60° C.). Squalane is added to the pre-mix non-aqueous formulation for the product not containing Mg Boroascorbate in its aqueous pre-mix.

After these two pre-mixes are prepared, heated and combined and the resulting mixture is stirred in order to achieve complete dispersion. It is then allowed to cool. Benzyl Alcohol, used as a preservative system, is added to the cooling dispersion before the addition of L-Carnosine and L-Theanine. To the resulting cooling dispersion, Vitamin K (powder), Colostrum (powder), Green Tea Extract-VDF and Cucumber are added. The last step is the addition of Dimethylethanolamine (DMEA) to adjust the pH.

Upon reaching room temperature, the resulting cream is packaged.

It will be apparent that modifications and variations within the scope of the present invention may be prepared and provided.

By working example, a formulation (Composition B) was prepared having 10% carnosine in an aqueous vehicle and the composition was buffered to pH 9.4 with dimethylaminoethanol. A formulation with a white creamy appearance was obtained. Subjects having facial skin wrinking were treated by applying 1-2 mL of the formulation topically twice per day for 3 to 4 weeks.

Subject 1 was a female, aged 40 years, whose face had fine lines and wrinkles After 4 weeks there was dramatic 40% wrinkle reduction around the eyes and the nasolabial folds as well as 30% wrinkle reduction at the upper tip area. The only observed or noticed side effect was a slight tingling sensation that disappeared after 2 days.

Subject 2 was a female, aged about 68, whose face had deep wrinkles and "crow's feet" around the eyes and nasolabial ibid area as well as the upper lip area. After 3 weeks the subject experienced 30% wrinkle reduction around the eyes and the upper lip. There were no side effects observed or noted.

Subject 3 was a female, aged about 39, whose face revealed early wrinkling. The subject after 4 weeks had 30% wrinkle reduction around the eyes and as well as having improved refined skin tone and lasting skin shininess, as well as reduced puffiness around the eyes.

Subject 4 was a male, aged about 38, whose face revealed early wrinkling. The subject used the formulation for 3 weeks and had 20% wrinkle reduction around the eyes along with improved skin smoothness. There were no side effects observed or noted.

Subject 5 was a female, aged about 40, whose face had a rash and irritation, most prominently on her forehead and cheeks as well as substantial wrinkling around the areas of the eyes and mouth. after 1 or 4 days but stopped due to the rash becoming aggravated. With the formulation, after about 4 weeks of the regimen, the rash was resolved and wrinkling reduced by 40% with improved evening of skin tone.

Subject 6 was a female, aged about 84, whose face was heavily wrinkled. The subject used the formulation for 4 weeks and had dramatic 35%-40% wrinkle reduction around the eyes and 30% wrinkle reduction on the upper lip. There were no side effects observed or noted.

Subject 7 was an adolescent female, aged 16, included in the test to determine possible side effects with young nonwrinkled skin. She experienced no side effects after 3 weeks when treated with Composition B and had acne cleared from her face.

A comparative formulation at pH 5.8 was also prepared (Composition A) and tested, but resulted in unacceptable side effects including erythrema, a burning sensation, and skin irritation. Surprisingly, regimented treatment with the alkalinized formulation (Composition B) described here was not associated with unacceptable side effects, skin irritation or burning sensation, and resulted in a significant reduction and reversal of pre-existing wrinkling of skin. No retinoid was incorporated in the formulation as used in these examples. The subjects used no other facial compositions other than soap during the period of treatment.

The invention claimed is:

1. A method for reducing the formation of products of glycation which method comprises applying a topical alkaline cosmeceutical composition at least twice a day for at least two weeks to a subject having a body part subject to glycation to reduce formation of glycation end products on said body part, said cosmeceutical composition comprising 0.5 to 50% by weight of an antiglycating agent selected from the group consisting of carnosine, homocarnosine, anserine, an n-acyl derivative of carnosine, an n-acyl derivative of homocarnosine, an n-acyl derivative of anserine, n-acetyl-carnosine and a complex salt thereof and mixtures thereof;

at least one additional agent compatible with said antiglycating agent, said additional agent being
0.1% to about 5% by weight of a tocotrienol or a mixture of 0.1 to about 5% by
weight of a tocotrienol and 0.1% to about 5% by weight of L-theanine and a cosmeceutical acceptable aqueous vehicle, wherein said cosmeceutical composition is alkalinized to a pH of 8.0 to 9.5.

2. The method of claim 1, wherein said alkalinizing basic component is selected from the group consisting of dimethylethanolamine, aminomethylpropanol, triethanolamine, monoisopropanolamine, alkaline water and mixtures thereof.

3. The method of claim 1, wherein said cosmeceutical composition is formulated as a daytime composition, a nighttime composition, a skin toning composition, or a perioorbital composition.

4. The method of claim 1, wherein said antiglycating agent is a mixture of carnosine and acyl-carnosine.

* * * * *